(12) United States Patent
Asafusa

(10) Patent No.: US 6,929,609 B2
(45) Date of Patent: Aug. 16, 2005

(54) ULTRASONIC DIAGNOSING/TREATING DEVICE AND METHOD THEREFOR

(75) Inventor: Katsunori Asafusa, Chiba (JP)

(73) Assignee: Hitachi Medical Corporation, Tokyo (JP)

(*) Notice: Subject to any disclaimer, the term of this patent is extended or adjusted under 35 U.S.C. 154(b) by 180 days.

(21) Appl. No.: 10/446,028

(22) PCT Filed: Jan. 18, 2002

(86) PCT No.: PCT/JP02/00339
§ 371 (c)(1),
(2), (4) Date: Jul. 11, 2003

(87) PCT Pub. No.: WO02/056957
PCT Pub. Date: Jul. 25, 2002

(65) Prior Publication Data
US 2004/0059219 A1 Mar. 25, 2004

(30) Foreign Application Priority Data
Jan. 18, 2001 (JP) ........... 2001-010607

(51) Int. Cl.⁷ .............. A61B 8/00
(52) U.S. Cl. ................ 600/439
(58) Field of Search .......... 600/407–472; 601/2–4; 424/9.5–9.52; 604/20, 22, 290, 424

(56) References Cited

U.S. PATENT DOCUMENTS

| | | | | |
|---|---|---|---|---|
| 6,077,225 A | * | 6/2000 | Brock-Fisher | 600/439 |
| 6,309,355 B1 | * | 10/2001 | Cain et al. | 600/439 |
| 6,340,348 B1 | * | 1/2002 | Krishnan et al. | 600/447 |
| 6,413,221 B1 | * | 7/2002 | Brock-Fisher | 600/458 |
| 6,428,477 B1 | * | 8/2002 | Mason | 600/437 |
| 6,475,148 B1 | * | 11/2002 | Jackson et al. | 600/439 |
| 6,776,761 B2 | * | 8/2004 | Ottoboni et al. | 600/458 |

* cited by examiner

*Primary Examiner*—Ali Imam
(74) *Attorney, Agent, or Firm*—Antonelli, Terry, Stout & Kraus, LLP (57) ABSTRACT

An ultrasonic diagnostic/treatment device includes a first ultrasonic wave irradiator that transmits a first ultrasonic wave signal to an organism for obtaining an image and receives a received wave signal corresponding to an echo signal of the first ultrasonic wave signal, a processor that processes the received wave signal to obtain diagnostic information, a second ultrasonic wave irradiator that irradiates the organism with a second ultrasonic wave signal for destroying medicine-containing microcapsules administered to the organism, and a controller that controls the second ultrasonic wave irradiator on the basis of the diagnostic information obtained by the first ultrasonic wave irradiator.

42 Claims, 8 Drawing Sheets

ULTRASONIC DIAGNOSING/TREATING DEVICE AND METHOD THEREFOR

CROSS-REFERENCE TO RELATED APPLICATION

This application is the U.S. National Phase under 35 U.S.C. § 371 on International Application PCT/JP02/00339, filed on Jan. 18, 2002, which claims priority of 2001-10607, filed Jan. 18, 2001.

TECHNICAL FIELD

The present invention relates to an ultrasonic diagnostic/treatment device and a method therefor, and in particular to an ultrasonic diagnostic/treatment device and a method therefor that are suited for intensively administering medicine to a diseased part in an organism.

BACKGROUND ART

In recent years, ultrasonic diagnostic/treatment devices used to treat diseased parts of bodies are being developed. There are several kinds of devices that use ultrasonic waves to treat diseased parts of organisms. A first kind of device uses ultrasonic waves to create an image of a diseased part and uses that image as a guide image for inserting a catheter or a needle into an organism. A second kind of device uses energy of ultrasonic waves emitted into the organism as energy to destroy the diseased tissue. A third kind of device irradiates ultrasonic waves to a medium administered inside the organism, the resulting change in the state of the medium causing destruction of the diseased tissue.

As an example of the third kind of conventional device, an ultrasonic diagnostic/treatment device is disclosed in JP-A-2000-189521 that is disposed with collecting means that irradiates the organism with a first ultrasonic wave signal for obtaining an echo image and collects received signals corresponding to the echo signals, image acquisition means that processes the echo signals to obtain image information, and irradiation means that sends to the organism a second ultrasonic signal for destroying microcapsules so that medicine included inside the microcapsules or microbubbles which have been administered to the organism is activated in a diseased part of the organism.

However, with respect to this conventional device, although there is description in regard to setting the emission direction of the second ultrasonic wave for destroying the microcapsules, no consideration is given in regard to controlling the second ultrasonic wave irradiation means in association with diagnostic information obtained by the first ultrasonic wave irradiation means.

The present invention was devised with the object of providing an ultrasonic diagnostic/treatment device that improves treatment efficiency.

The present invention was also devised with the object of providing an ultrasonic diagnostic/treatment device with which the destruction status of microcapsules can be visually confirmed, and the amount of medicine sealed in the microcapsules which is administered to the diseased part can be confirmed.

The present invention was also devised with the object of providing an ultrasonic diagnostic/treatment device with which the efficiency of treatment can be further improved by the administration of plural microcapsules.

DISCLOSURE OF THE INVENTION

In order to achieve the above-described objects, an ultrasonic diagnostic/treatment device according to the invention includes: first ultrasonic wave irradiation means that transmits to an organism a first ultrasonic wave signal for obtaining an image and receives wave signals corresponding to echo signals of the first ultrasonic wave signal; means that processes the received wave signals to obtain diagnostic information; second ultrasonic wave irradiation means that irradiates the organism with a second ultrasonic wave signal for destroying microcapsules containing medicine and administered to the organism; and control means that controls the second ultrasonic wave irradiation means on the basis of the diagnostic information obtained by the first ultrasonic wave irradiation means.

In order to administer to a diseased part medicine encapsulated in microcapsules by destroying the microcapsules, ultrasonic waves are transmitted to the microcapsules at the time that the microcapsules have arrived at the diseased part, and the microcapsules are destroyed. An operator confirms that the microcapsules are concentrated near the diseased part and based on ultrasonic waves received for image diagnosis controls ultrasonic wave radiation that destroys the microcapsules. Thus, treatment efficiency, including treatment time, is improved. Also, the amount of time that the patient must be restrained is also reduced due to the treatment time being reduced, and the amount of microcapsules administered to the patient can be reduced. Here, the time at which the microcapsules have arrived at the diseased part may be considered to be the time at which the concentration of microcapsules that have circulated to the diseased part reaches an optimum level.

Image display means which display undestroyed microcapsules as detected by the first ultrasonic wave signals when the the second ultrasonic wave signal is switched to the first ultrasonic wave signal are also disposed.

The destruction status of the microcapsules is visually confirmed by a doctor. The destruction status of the medicine-containing microcapsules is visually confirmed, and the extent to which the medicine encapsulated in the microcapsules has been administered to the diseased part can be confirmed.

Also included are: first ultrasonic wave irradiation means that transmits, to an organism to which at least two different types of medicine-containing microcapsules have been administered, a first ultrasonic wave signal for obtaining an image and that receives a received wave signal corresponding to the echo signal of the first ultrasonic wave signal; means that processes the received wave signal to obtain diagnostic information; second ultrasonic wave irradiation means that irradiates the organism with a second ultrasonic wave signal for destroying the microcapsules administered to the organism; and control means that controls the second ultrasonic wave irradiation means on the basis of the obtained diagnostic information.

When numerous types of microcapsules in which different medicines have been encapsulated are used, the second ultrasonic waves are irradiated to one type of microcapsules at the time at which those microcapsules have arrived at the diseased part so that those microcapsules are destroyed. By administering plural types of microcapsules, the efficiency of treatment is further improved.

BEST MODE FOR CARRYING OUT THE INVENTION

An embodiment of the invention will be described in detail below on the basis of the attached drawings.

Figure 1:
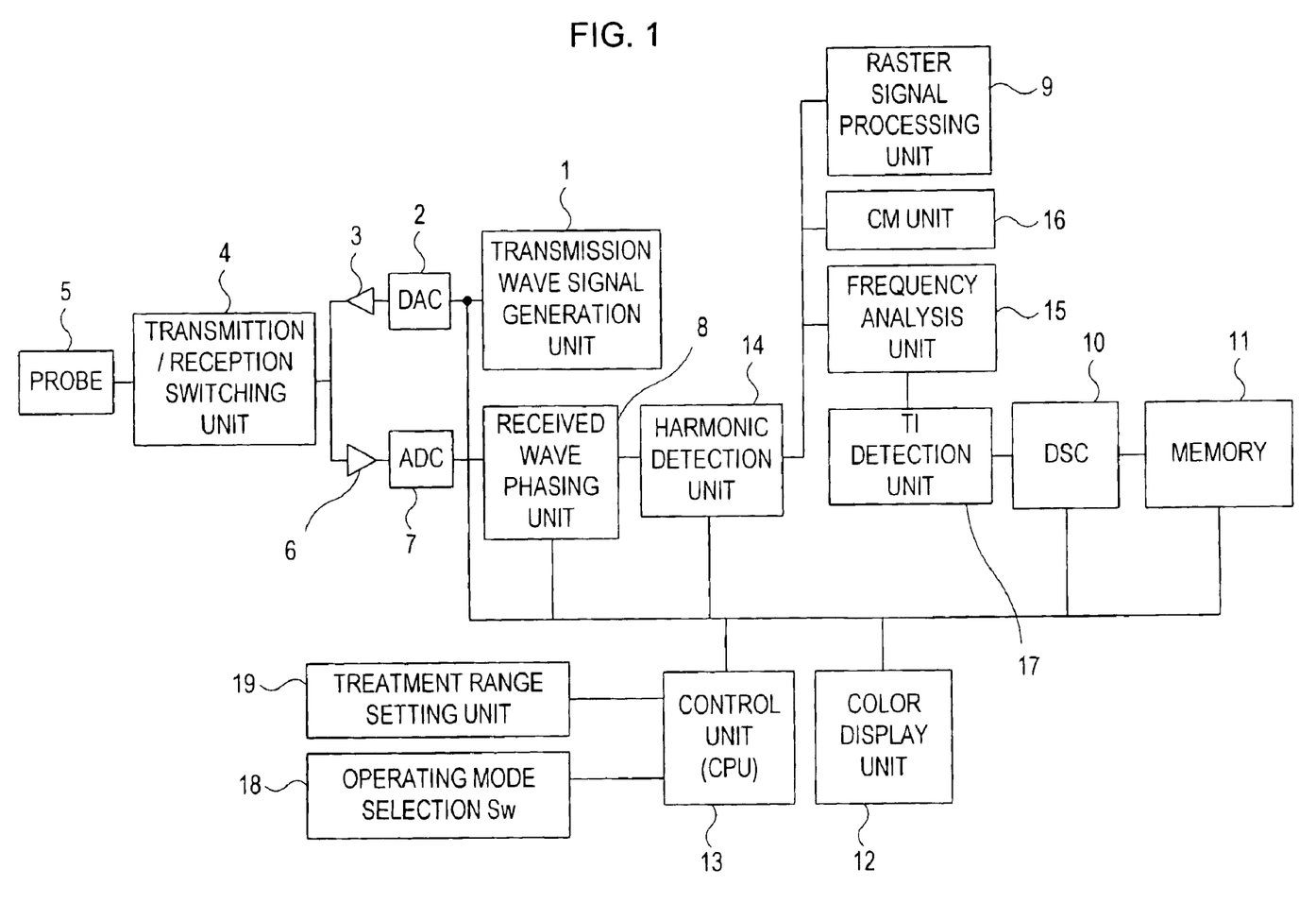
FIG. 1 is a block diagram showing the entire configuration of an embodiment of an ultrasonic diagnostic/treatment device preferable for applying the invention.

FIG. 1 is a block diagram showing the configuration of an ultrasonic diagnostic/treatment device according to the invention.

In FIG. 1, a transmission wave signal generation unit 1 drives an ultrasonic probe and generates a digital drive signal for generating ultrasonic waves and are transmitted inside the body of a patient. A DA converter (DAC) 2 converts the drive signal outputted from the transmission wave signal generation unit 1 to an analog voltage signal. A transmission wave amp 3 amplifies and outputs the signal inputted from the DAC 2. A transmission/reception switching unit 4 passes a signal from a transmission wave circuit unit to the probe when the ultrasonic waves are to be transmitted and passes an echo signal received by the probe to the received wave processing unit when the ultrasonic waves are received. An ultrasonic probe 5 transmits ultrasonic waves to the body of a patient undergoing treatment and receives ultrasonic waves (echo) reflected inside the body of the patient. The ultrasonic probe 5 can transmit and receive different plural ultrasonic waves—as an ultrasonic treatment device, it produces ultrasonic waves having a frequency and an energy level that destroys microcapsules and as an ultrasonic imaging device, it produces and receives ultrasonic waves having a frequency and an energy level that obtains an image of the inside of the patient's body.

A received wave amp 6 amplifies signals that are received by the probe 5 as the echo signals from the organism. An AD converter (ADC) 7 AD—converts the echo signal outputted from the received wave amp 6. A phasing unit 8 conducts phasing in which a received wave beam signal is formed. The number of channels of the received wave amp 6, the ADC 7 and the phasing unit 8 are equivalent to the number of oscillators that are operated when the ultrasonic probe 5 receives the waves, and an adding circuit is disposed at a terminal end of the phasing unit 8. The received wave beam signal is formed by these portions. It should be noted that the ADC 7 can also be considered to be part of the phasing unit 8.

A signal processing unit 9 administers preprocessing—namely, logarithmic compression, detection, filtering and enhancement—for imaging the echo signals inputted from the phasing unit 8. A digital scan converter 10 conducts conversion between the scan of the ultrasonic wave beam and a scan for image display. A display-use memory 11 stores the output of the digital scan converter 10. A color display device 12 comprises, for example, a color CRT display or a color liquid crystal display device. A control unit (CPU) 13 controls the above-described configuration requirements. The above configuration is substantially the same as the configuration of known ultrasonic diagnostic medical image devices.

The ultrasonic diagnostic/treatment device according to the invention has, in addition to the function of obtaining a diagnostic image as described above, the function of destroying microcapsules inside the body of a patient, the function of detecting and imaging the destruction status of the microcapsules, and the function of determining the timing for destroying the microcapsules. Next, component parts of the present embodiment that are added to the above-described configuration in order to achieve the latter three functions will be described.

Figure 2:
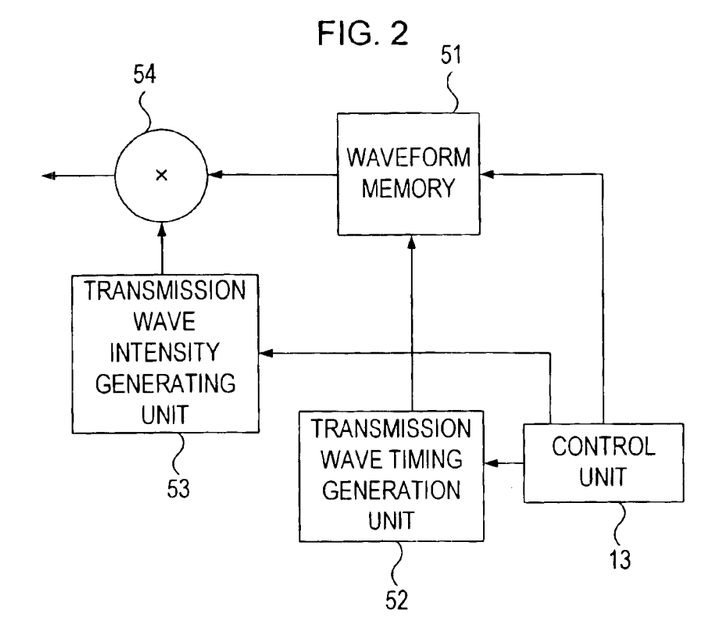
FIG. 2 is a block diagram showing the configuration of a transmission wave signal generation unit shown in FIG. 1.

First, the component part that fulfills the function of destroying the microcapsules will be described. FIG. 2 is a block diagram showing the detailed configuration of the transmission wave signal generation unit 1 shown in FIG. 1. In FIG. 2, a waveform memory 51 stores the frequency of the transmission wave, and in this waveform memory 51 are stored the frequency of an ultrasonic wave used at the time the diagnostic image is acquired and the frequency used at the time the microcapsules are to be destroyed. Here, plural frequencies for destroying the microcapsules are stored in the waveform memory 51 so that numerous types of microcapsules can be destroyed. A transmission wave timing control unit 52 phase-controls or delay-controls the output signals and outputs them respectively to each of the plural oscillators housed in the probe 5, so that the ultrasonic waves transmitted from the probe 5 are focused on the diseased part of the body. A transmission wave intensity control unit 53 controls the intensity of the transmission wave signal outputted from the waveform memory 51. A multiplier 54 multiplies the signal outputted from the transmission wave intensity control unit 53 with the signal outputted from the waveform memory 51. The above configuration requirements are controlled by the CPU 13. The frequency and intensity of the ultrasonic wave by which the microcapsules are destroyed which varies in accordance with the type of microcapsules, and the destruction order of the microcapsules, are programmed and incorporated in the CPU 13 in advance.

Generally, the transmission wave intensity P1 used in ultrasonic diagnosis is 0<P1 1[W/cm$^2$]. A transmission wave intensity P2 that can destroy microcapsules is 0<P2 5[W/cm$^2$]. The relation between the transmission wave intensities is P1=m×P2 (where m is 0<m 0.2).

Next, the configuration for observing the destruction status of the microcapsules will be described. Prior to destroying the microcapsules, their concentration in the diseased part was detected, and after the microcapsules have been destroyed, the destruction status can be seen by the extent to which microcapsules remaining that have not been destroyed. When undestroyed microcapsules are irradiated with the ultrasonic waves, a resonance phenomenon arises, capsule films are destroyed, and a frequency that is different from the frequency of the ultrasonic waves transmitted at that time is generated. The "frequency that is different"

referred to here includes many harmonic components having frequencies with different from the frequency of the transmitted ultrasonic waves. By imaging the harmonic components, the destruction status of the microcapsules can be observed. The configuration by which the harmonic components are imaged will be described using FIG. 1. In FIG. 1, the harmonic detection unit 14 detects the echo signal of the harmonic that the microcapsules, which have been irradiated with the ultrasonic waves and destroyed inside the body of the patient, generate. The frequency analysis unit 15 conducts frequency analysis of the harmonic echo signal detected by the harmonic detection unit 14. The color mapping unit 16 determines spatial distribution of the components of the harmonic outputted from the frequency analysis unit 15, adds color information to the determined spatial distribution, and outputs this.

Next, an example of the detailed configurations of the harmonic detection unit 14 and the frequency analysis unit 15 will be described using FIG. 3. The harmonic detection unit 14 comprises a local oscillator 141, multipliers 142 and 143, and low-pass filters (LPF) 144 and 145. Here, the local oscillator 141 is configured by a memory and a counter and outputs two local signals—i.e., $\sin(2\delta ut)$ and $\cos(2\delta ut)$—in which a phase for shifting the frequency of the echo signal is shifted by $\delta/2$ rad, and the multipliers 142 and 143 multiply the inputted echo signal with these local signals and frequency-shift the fundamental frequency component included in the echo signal, i.e., the frequency of the ultrasonic waves transmitted from the probe, and the harmonic component generated when the microcapsules are destroyed. The LPFs 144 and 145 contain registers and multiplication/addition computing units and, applied to the fundamental wave frequency component and the harmonic component frequency-shifted by the multipliers, remove the fundamental frequency component and pass the harmonic component.

The frequency analysis unit 15 comprises a fast Fourier transform (FFT) computing unit 151 and an absolute value (ABS) computing unit 152. The FFT computing unit 151 includes a well-known butterfly multiplier, and converts the echo signal from a real-time array to a frequency array, and the ABS computing unit 152 comprises a squaring computing unit, an addition computing unit and a square root computing unit, and calculates the signal intensity of each frequency outputted from the FFT computing unit 151.

Figure 4:
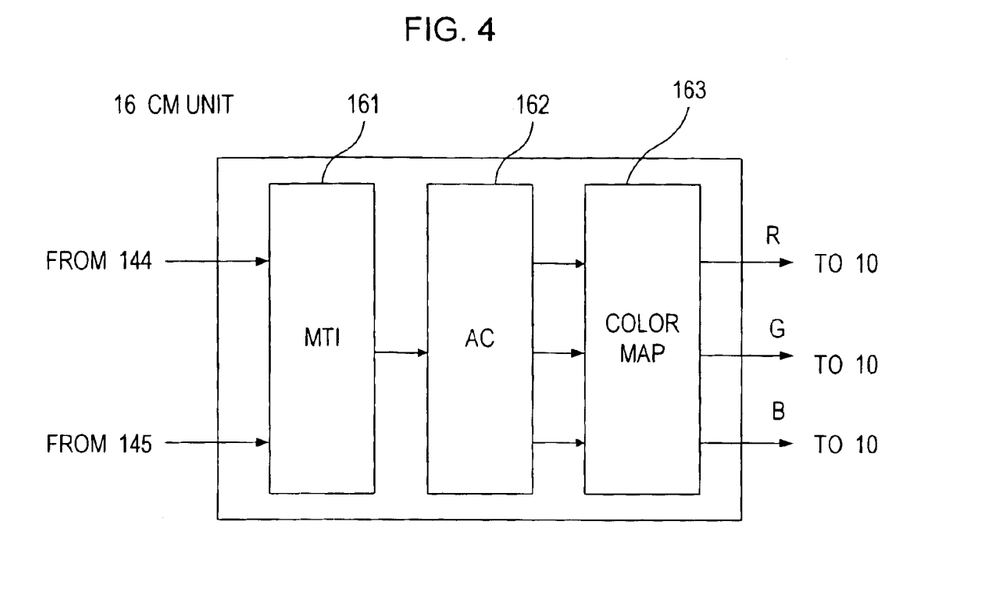
FIG. 4 is a block diagram showing the configuration of a color mapping (CM) unit shown in FIG. 1.

Next, the configuration for achieving the function of calculating the time of the destruction of the microcapsules will be described. Microcapsules injected into a vein are circulated inside the organism and carried to the diseased part by the flow of blood. At this time, the concentration of microcapsules that have reached the diseased part becomes greater with time and, thereafter, becomes less with time. Therefore, when the concentration of microcapsules changing with the elapse of time is observed, the proper irradiation timing of the ultrasonic waves to destroy the microcapsules can be calculated. In the present embodiment, the color mapping (CM) unit 16 is disposed in order to grasp changes in the concentration of the microcapsules in the diseased part. As shown in FIG. 4, the CM unit 16 comprises an MTI (Moving Target Indication) filter 161, an autocorrelation computing unit 162 and a color map creation unit 163. The MTI filter 161 comprises a register, a comparator, a band-pass filter (BPF) and the like, and is used in the field of bloodstream distribution image measurement using the Doppler phenomenon as in radar and ultrasonic diagnostic devices, distinguishes from surrounding tissue in which there is no movement the microcapsules flowing to the diseased part and measures these microcapsules. The autocorrelation computing unit 162 has a computing unit such as a DSP (Digital Signal Processor) and a memory, and computes by autocorrelation computation the moving speed of the microcapsules, speed dispersion and signal intensity. The autocorrelation technology is also well known in the field of ultrasonic diagnostic devices. The color map creation unit 163 comprises a memory and a color encoder, writes data inputted from the autocorrelation computing unit 162 in its memory, converts the data to image data, and adds, by color encoding, color information corresponding to these values to these data.

Figure 5:
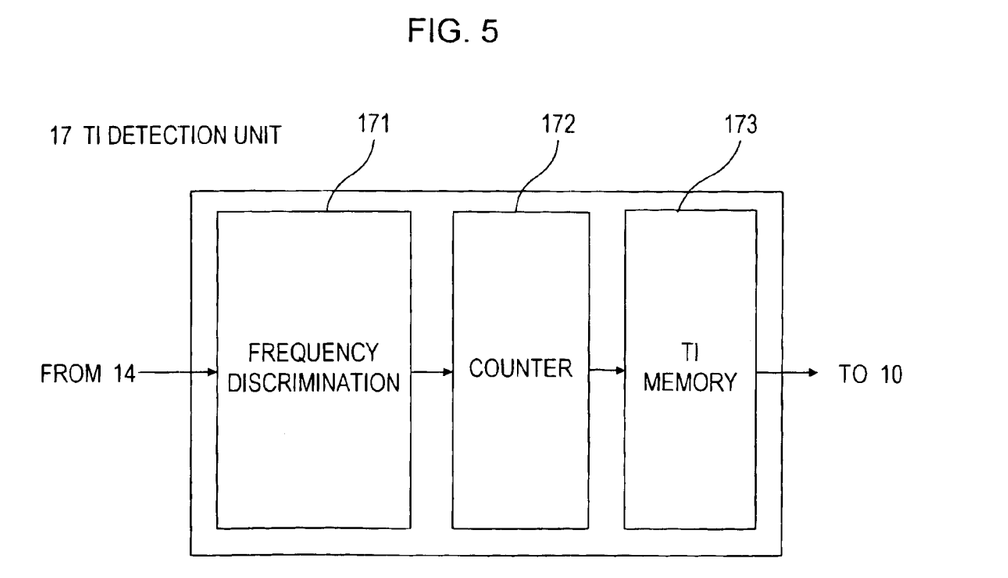
FIG. 5 is a block diagram showing the configuration of a time intensity (TI) detect ion unit shown in FIG. 1.

Next, the configuration for achieving the function of grasping the destruction status and the flow status of the microcapsules to the diseased part will be described. In the present invention, it is easy for a doctor to grasp the destruction status and the flow status of the microcapsules to the diseased part by not only displaying these for that moment, but also changes in these over time. In the present embodiment, the time intensity detection unit 17 is disposed for this purpose as one configuration example. As shown in FIG. 5, the time intensity detection unit 17 comprises a frequency discrimination circuit 171 that inputs a signal from the harmonic detection unit 14 and discriminates and outputs the signal for each frequency, a counter circuit 172 that counts the output of the frequency discrimination circuit 171 for each frequency, and a time intensity memory (TI memory) 173 that converts the output of the counter circuit 172, by command of the CPU 13, to a time distribution of the signal with frequency as a parameter, one axis showing time and the other showing signal value. The time intensity detection unit 17 configured as described above enables the temporal changes in the signal appearance information of each harmonic component within a certain predetermined period of time to be displayed as a graphic. It should be noted that the memory in the DSC 10 can also be used for the TI memory 173.

By establishing a switch for adjusting the transmission intensity of the ultrasonic waves for destroying the microcapsules in the form of an operation mode selection switch, the transmission intensity can be adjusted to match the physical constitution of the patient while observing the destruction status of the microcapsules. Because by the adjustment switch makes it possible to control the transmission intensity as much as possible while the treatment is being carried out, ultrasonic treatment that reduces the burden on the patient resulting from the treatment is possible.

Next, the operation of the ultrasonic diagnostic/treatment device configured set forth above will be described. Initially, the doctor makes preparations for injecting the microcapsulated medic ine into a vein of the patient. An automatic injector can be used to inject the medicine. When the preparations have been finished, the doctor turns on the power to the ultrasonic diagnostic/treatment device and uses the imaging function of the device to display an ultrasonic tomogram of the treatment area on the monitor of the device, and, by observing the tomogram, specifies the position of the probe at which the treatment area is best displayed.

Imaging of the ultrasonic tomogram for this purpose is conducted as follows. The doctor first selects a tomogram imaging mode with an operation mode selection switch 18 of the device disposed on the control panel of the ultrasonic diagnostic/treatment device. Then, the doctor touches the probe 5 to the outer surface of the treatment area of the patient, operates ultrasonic scanning initiation switch (not illustrated) and operates a focus depth setter in order to set the focus depth of the ultrasonic waves transmitted from the probe. In doing so, a command is sent from the CPU 13 to the transmission wave signal generation unit 1, and the transmission wave signal generation unit 1 generates digital transmission wave pulse signals for imaging the tomogram to which are added a predetermined delay time for the pulse supplied to each oscillator so that these ultrasonic wave pulses will be concentrated (meaning the same as "be in phase") at the set focus depth.

The transmission wave pulse signals outputted from the transmission wave signal generation unit 1 are converted to analog signals in the DAC 2 and inputted to the transmission wave amp 3. The transmission wave pulse signals are amplified by the transmission wave amp 3 to a voltage necessary to induce piezoelectric vibration in the oscillators, and supplied to the probe 5 by the transmission/reception switching unit 4. The transmission wave pulse signals that have been delayed by the predetermined delay time are applied to the oscillators of the probe 5, and the ultrasonic waves are transmitted to the subject organism from the oscillators time intervals corresponding to these delay times. Thus, the ultrasonic waves transmitted inside the subject organism are propagated inside the subject organism so that they concentrate (meaning the same as "come in phase") at the set focus depth, and also some of the ultrasonic waves are reflected back toward the probe as an echo at the boundaries of different acoustic impedances inside the subject organism.

The probe 5 receives the echo, converts it to an electrical signal, and outputs it. The receiving operation of the probe 5 is conducted by all of oscillators conducting the transmission operation or a part thereof, and the signals received by the oscillators are individually inputted to the received wave amp 6 via the transmission/reception switching unit 4, amplified in the received wave amp 6, and thereafter converted to digital signals in the ADC 7 and outputted to the received wave phasing unit 8. The received wave phasing unit 8 is controlled by the CPU 13 and conducts dynamic focusing by addition processing and delay control with respect to each received wave signal. In this way it continuously changes its focal point along a predetermined path inside the organism and captures the ultrasonic wave echoes from each focal point. Ultrasonic wave beam signals on a predetermined line inside the subject organism are obtained by the above transmission and receiving operations.

The ultrasonic wave beam signals outputted from the received wave phasing unit 8 are inputted to the Raster signal processing unit 9, undergo logarithmic compression, detection, dynamic filtering and enhancement, and are outputted to the DSC 10. Harmonic signals of a weak intensity including a frequency of an integral multiple of the ultrasonic wave frequency transmitted from the probe 5 into the organism is included in the signals inputted to the Raster signal processing unit 9, but these are removed by filtering. The signals inputted to the DSC 10 are stored at a predetermined address in the memory for the purpose of image formation. When the above ultrasonic wave transmission and receiving operations are repeatedly conducted while successively shifting the ultrasonic wave beam direction and an image is formed in the memory of the DSC 10, the image data thereof is read in synch with scanning of the color display device 12 via the display memory 11 and preferably displayed in black and white on the display screen of the color display device 12 as an ultrasonic tomogram. The ultrasonic scanning inside the subject organism is continuously conducted even after one frame image is obtained, and acquisition and display of a tomogram at a frame rate of about 30 frames per second are conducted.

While continuing the ultrasonic scanning, the doctor changes the position and the contact angle of the probe 5 with respect to the surface of the organism to locate the diseased part that is to be treated. Then, the doctor retains the probe 5 at the position at which the diseased part to be treated is best displayed on the color display device 12, operates a freeze switch (not shown) and freezes the image display. It should be noted that a retaining tool can be used to retain the probe.

The doctor observes the frozen image displayed on the color display device 12 and designates the treatment area. A technique for setting the scanning range using color flow mapping (CFM) which gives a two-dimensional display of the flow of blood can be applied for the designation of the treatment area, and the designation of the treatment area is set by a treatment range setter 19 by designation of the scanning range of the ultrasonic beam during treatment, and this designation signal is stored in the CPU 13. The reason for setting the ultrasonic wave beam scanning range for treatment using the frozen tomogram is because there is no spare time for conducting that operation when moving from graphing of the microcapsules, which is conducted next, to the treatment.

In this state, the doctor or an assistant injects the microcapsules in which the medicine is encapsulated into a vein of the patient using an injector. Because the microcapsules injected into the vein flow to the diseased part circulating through the patient's body in a few seconds after the injection, the doctor operates the operation mode selection switch 18 and switches from the tomogram acquisition mode used up to that time to a graphing mode. When this switching signal is inputted to the CPU 13, the CPU 13 sends an activation command to the harmonic detection unit 14, the frequency analysis unit 15, the color mapping unit 16, and the time intensity (TI) detection unit 17. When the mode has been switched from the tomogram acquisition mode to the graphing mode, is it preferable for the frequency of the ultrasonic waves transmitted from the probe 5 to the inside of the patient's body to be changed to a value that can best detect the microcapsules injected into the patient's body.

When this changing command is received, the transmission wave signal generation unit 1 out puts a transmission wave pulse. This transmission wave pulse is successively supplied to the DAC 2, the transmission wave amp 3, the transmission/reception switching unit 4, and the probe 5, and the ultrasonic waves are transmitted from the probe 5 to the diseased part. Similar to the imaging of the tomogram above, scanning is repeatedly conducted while changing the direction of each transmission wave so that the entire region is scanned. Below, the receiving operation thereof will next be described.

Figure 6:
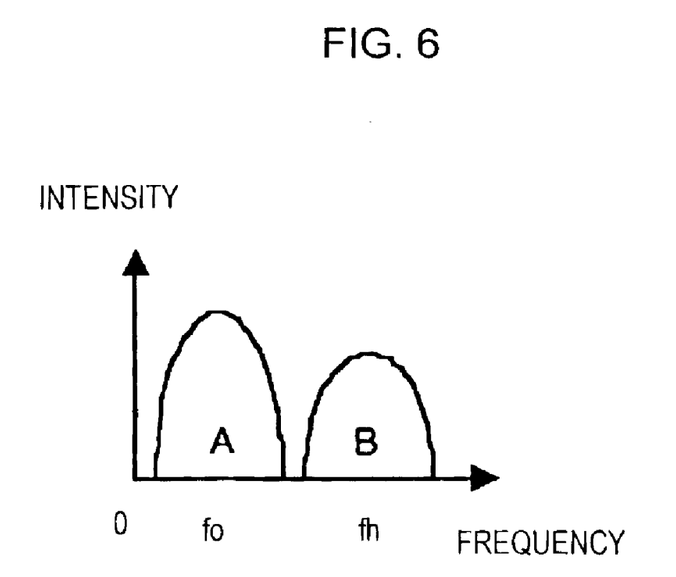
FIG. 6 is a graph showing frequency distributions of a fundamental wave $f_o$ and a harmonic $f_h$.
Figure 7:
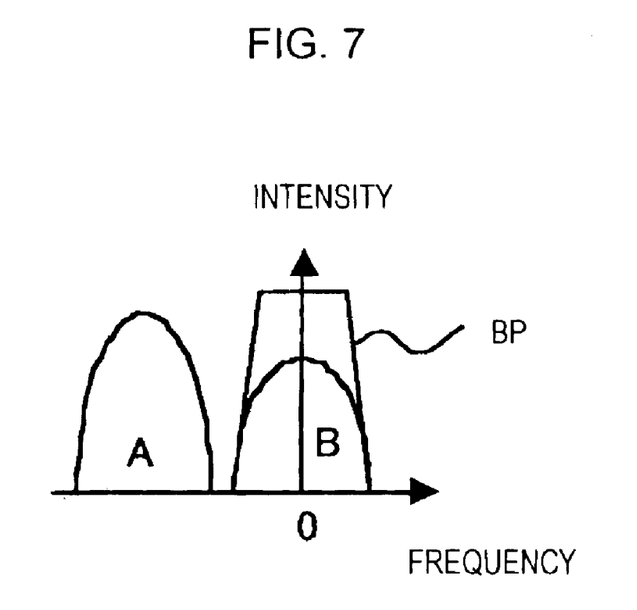
FIG. 7 is a graph showing frequency distribution of output signals of the harmonic detection unit.

The received wave echo signal of the ultrasonic wave transmitted in a certain direction from the probe 5 is inputted to the Raster signal processing unit 9 and the harmonic detection unit 14 via the probe 5, the transmission/reception switching unit 4, the received wave amp 6, the ADC 7, and the received wave phasing unit 8. As shown in FIG. 6, the echo signal inputted to the Raster signal processing unit 9 and the harmonic detection unit 14 includes a signal A, which has a certain band and whose center frequency corresponding to the frequency transmitted from the probe 5 is $f_o$, and a harmonic signal B, which has a certain band and whose center frequency is a frequency $f_h$ of an integral multiple of the center frequency $f_o$. The signal including the signal A and the harmonic signal B inputted to the harmonic detection unit 14 are respectively multiplied in the multipliers 142 and 143 by a local (reference) signal $\cos(2\delta ft)$ and $\sin(2\delta ft)$ outputted from the local oscillator 144 and frequency-shifted as shown in FIG. 7. Then, an echo signal comprising the harmonic signal B is extract ed from these frequency-shifted signals by the LPFs 144 and 145 which have a band pass (BP), and this signal is outputted to the frequency analysis unit 15 and the color mapping unit 16.

After the signal A and the harmonic signal B inputted to the Raster signal processing unit 9 have undergone preprocessing for imaging similar to the echo signal processing during imaging for locating the diseased part, they are inputted to the memory of the DSC 10 in order to form a tomogram resulting from the signal A.

Then, the beam signal comprising the harmonic signal B inputted to the frequency analysis unit 15 is frequency-analyzed by sequential Fourier conversion in the FFT computing unit 15. The output of the frequency analysis unit 15 represents a frequency distribution of the harmonic signal B from a shallow part to the deep part of one signal beam. Because the harmonic signal generated at the time the microcapsules are irradiated with the ultrasonic waves is already known in advance by measurement, it can be known whether or not the microcapsules are flowing in the beam direction by observing the output of the frequency analysis unit 15. Then, the output of the frequency analysis unit 15 is inputted to the ABS computing unit 25, the signal intensity of the harmonic signal B successively inputted by the aforementioned configuration is calculated, the signal is separated according to frequency, and the signals are outputted to the TI detection unit 17.

Figure 8:
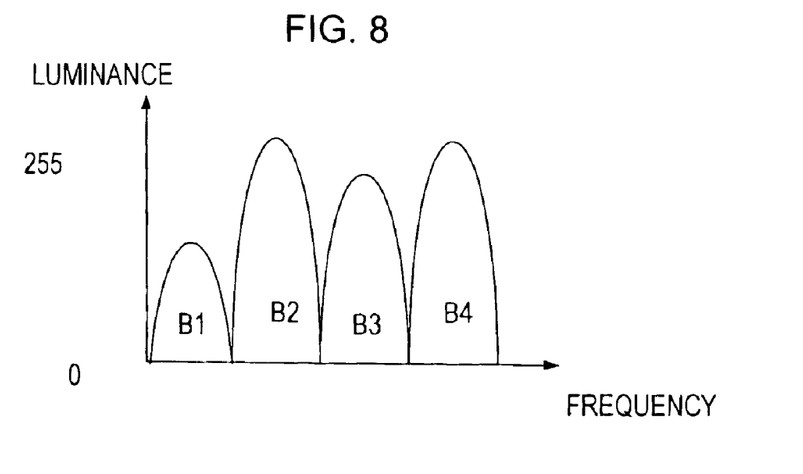
FIG. 8 is a graph showing frequency-discriminated signals outputted from the TI detection unit.

The signal representing the signal intensity for each harmonic frequency calculated by the ABS computing unit 152 in this manner is outputted to the TI detection unit 17, added to each frequency as shown in FIG. 8 in the counter circuit 172 of the TI detection unit 17, and stored in the memory in the DSC 10. Then, the data stored in the memory of the DSC 10 is provided in order to create the time intensity curve (TIC) shown in FIG. 9. The method of creating this TIC will be described in detail later.

The harmonic echo signal outputted from the harmonic detection unit 14 to the color mapping unit 16 is inputted to the MTI filter 161 and temporarily stored in a storage unit such as an internal register. The MTI filter is well known in the field of radars and the field of ultrasonic Doppler measurement, and is used in order to cancel information of a stationary part and detect only information of a moving object. In the present invention, the MTI filter 161 is for detecting moving information of the microcapsules or flow of blood flowing through the diseased part. In the MTI filter 161, it is necessary to transmit the ultrasonic wave beam in the same direction at least two times in order to detect only the movement of the microcapsules or the flow of blood.

Thus, when the receiving operation is concluded, the CPU 13 repeats the transmission and receiving operations without changing the ultrasonic wave transmission and reception direction. When the echo signal resulting from the second reception is inputted to the MTI filter 161 via the harmonic detection unit 14, computation of the difference between the data temporarily retained in the storage unit such as the register and the newly inputted data is conducted in the MTI filter 161, and the movement of the microcapsules or the flow of blood between these two transmissions and receptions is measured. Then, this information is provided for autocorrelation computation in the autocorrelation computing unit 162, and respective data of the moving speed, speed distribution, and signal intensity of the microcapsules or flow of blood is computed. These computed data are outputted to the color mapping unit 163, and information of the three primary colors of R (red), G (green) and B (blue) light is added to each of the data and stored in the memory of the DSC 10. Thus, through the transmission and reception of the ultrasonic wave beam in one direction, the frequency distribution along the beam and the moving information of the moving body are obtained.

Next, in order to two-dimensionally expand the acquisition of the information on movement of the moving bodies and the frequency distribution, transmission and reception are repeatedly conducted while successively shifting the direction of the ultrasonic wave beams, and a cross section including the diseased part is ultrasonically scanned. Due to this ultrasonic scanning, the TI detection unit 17 measures the frequency distribution in the cross section, and the color mapping unit 16 measures the movement of the microcapsules or the flow of blood in the cross section. Of these, the frequency distribution data detected by the TI detection unit 17 and stored in the memory of the DSC 10 are counted up for each frequency by the counting function of the CPU 13. The data counted for each frequency represent the integrated value of luminance per frequency with regard to a signal appearing in the ultrasonic scanning surface in a certain time of the time intensity curve shown in FIG. 9.

The movement information of the microcapsules or the flow of blood measured by the color mapping unit 16 is made into two-dimensional image data in the memory of the DSC 10, read out in order to visualize the moving status of the fluid in the cross section, outputted from the Raster signal processing unit 9, synthesized in the display memory 11 with the black-and-white image data made into two-dimensional image data in the memory of the DSC 10, and displayed on the color display device 12. By viewing this image, an operator can observe, virtually in real time, the microcapsules mixed in the flow of blood and flowing to the diseased part by color changes on the image.

Figure 9:
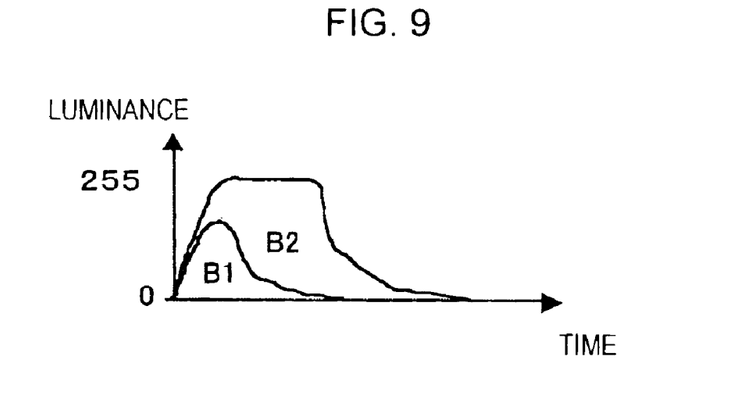
FIG. 9 is a graph showing a displayed time intensity curve.

The above transmission and receiving operations are repeatedly conducted thereafter, and the display of the tomogram and the color mapping image is updated each time the transmission and reception of the ultrasonic wave beam in one direction is completed and the memory content of the DSC 10 is updated. At the same time, the measurement data of the TI detection unit 17 are tallied each time scanning of one frame is completed, and the time intensity curve is created to match the measurement data of the preceding frames. The time intensity curve uses time for the horizontal axis, luminance for the vertical axis, and frequency as the parameter, and, as shown in FIG. 9, as the microcapsules gradually flow to the diseased part, the flow becomes a maximum at a certain time, and thereafter the amount decreases, and this is displayed as a graph.

The operator observes this graph, pays attention to the curve of a certain frequency generated when the microcapsules in which the medicine is encapsulated continuously flow to the diseased part, and when the doctor determines that the time has been reached when the microcapsules should be destroyed, the doctor switches the operation mode selection switch 18 on the ultrasonic diagnostic device to the treatment mode. Upon doing so, the CPU 13 sends a command for generating ultrasonic waves for treatment to the transmission wave signal generation unit 1 and the transmission wave amp 3. The transmission wave signal generation unit 1 receiving this command of the CPU 13 outputs a transmission wave pulse for transmitting ultrasonic waves having an ultrasonic frequency for destroying the microcapsules from the probe 5 to the inside of the patient's body, and the transmission wave amp 3 amplifies the transmission wave pulse inputted via the DAC 2 to a level that can destroy the microcapsules and outputs the transmission wave pulse. Because the amplified transmission wave pulse is delay-controlled in the transmission wave signal generation unit 1 so that the ultrasonic waves are focused at the endmost portion of the scanning range set as the treatment area in the ultrasonic wave transmission/reception direction (initial direction), the ultrasonic waves radiated from the oscillators of the probe 5 are focused at the treatment area of the patient.

Figure 10:
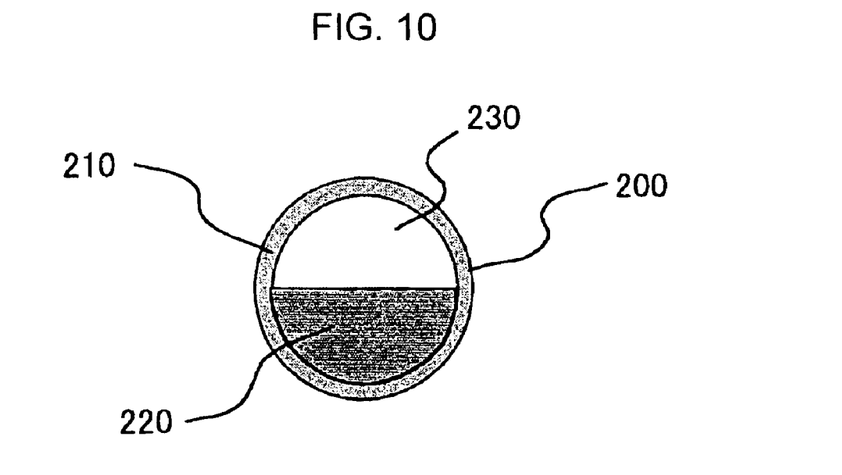
FIG. 10 is a conceptual diagram of a microcapsule.
Figure 11A:
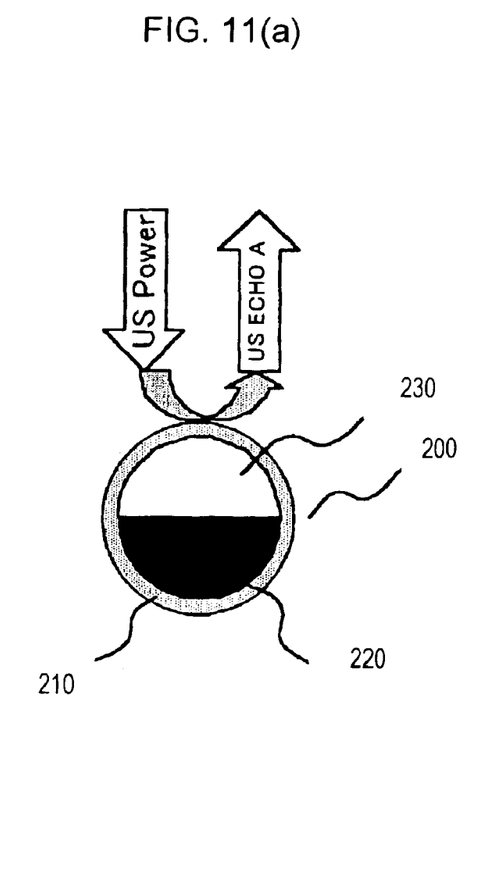
FIG. 11 are diagrams showing the behavior of a microcapsule that has been irradiated with ultrasonic waves.
Figure 11B:
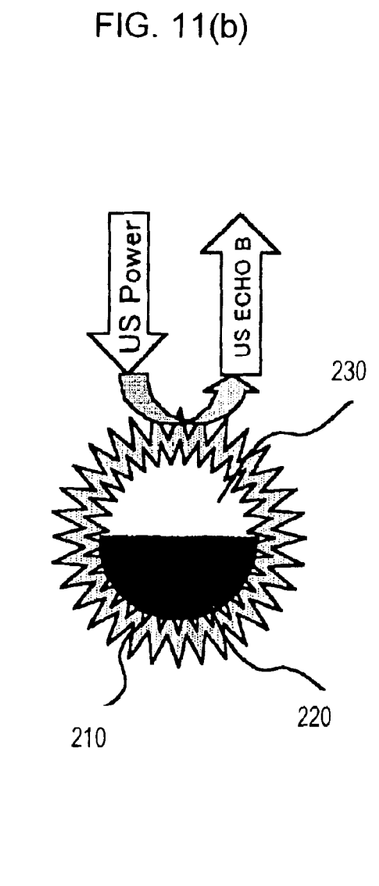
Figure 11C:
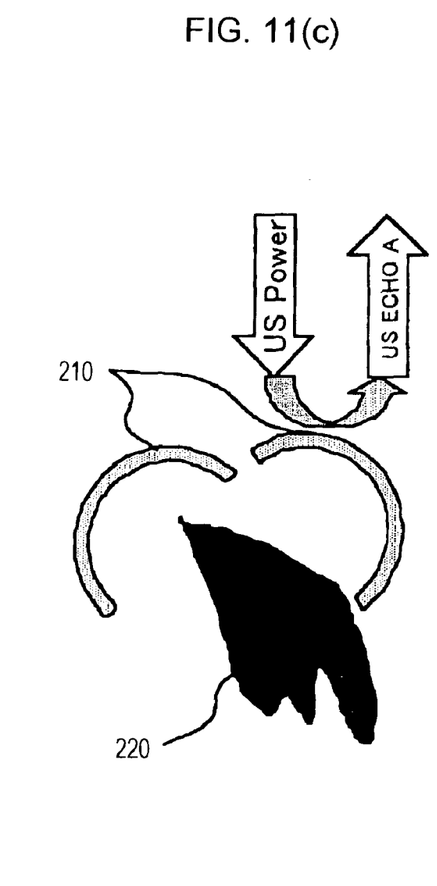
Figure 12A:
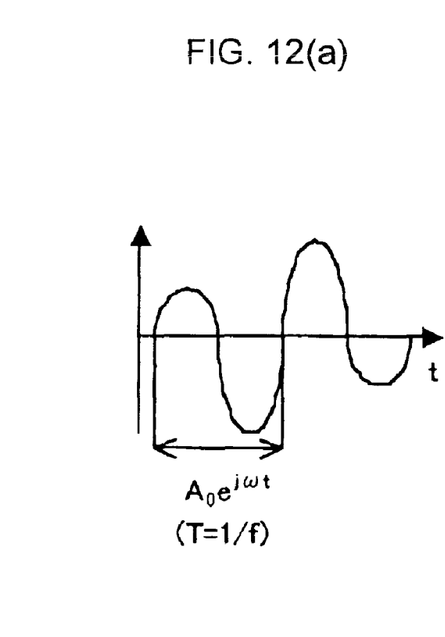
FIG. 12 are graphs showing waveforms of ultrasonic waves irradiated to the microcapsule and echo signals thereof.
Figure 12B:
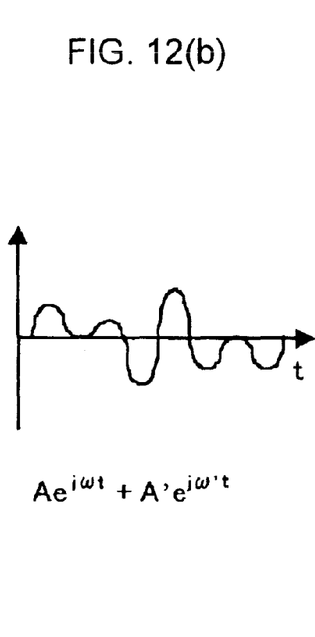
Figure 12C:
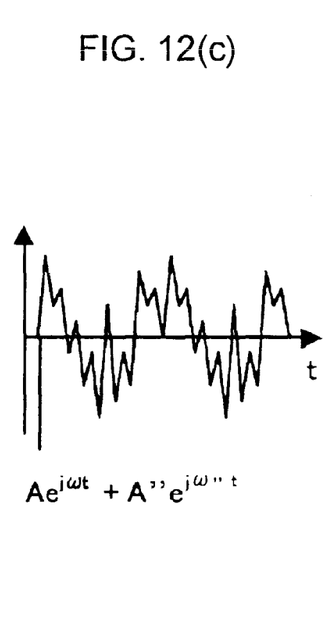
Figure 12D:
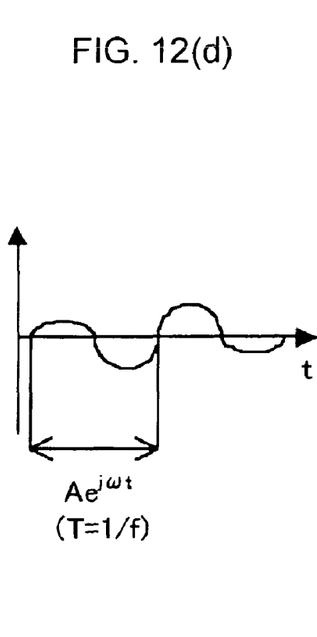

As shown in FIG. 10, an ultrasonic wave microcapsule 200 is a microcapsule in which a medicine 220 is encapsulated in a capsule shell 210, and a gas such as air is encapsulated inside the shell 210 together with the medicine 220. The destruction of the microcapsule 200 is dependent on the strength and diameter of the shell 210, and the resonance frequency of the microcapsule 200 is dependent on the diameter thereof. The microcapsule 200 is destroyed most effectively when the ultrasonic wave transmission frequency is this resonance frequency, and a resonance frequency f by which the microcapsule 200 is destroyed can be determined by the following equation 1.

$$f=(\tfrac{1}{2}\delta r)\times(3k\times P/\tilde{n}) \quad (1)$$

r: shell radius
k: specific heat ratio
P: internal pressure of shell
ñ: specific gravity Here, the behavior of the microcapsule 200 when the ultrasonic wave is irradiated to the microcapsule 200 will be described using FIGS. 11 and 12. When an ultrasonic wave of a waveform such as the one shown in FIG. 12(*a*) is transmitted to the microcapsule 200 (FIG. 11(*a*)), an echo including a two-dimensional harmonic component such as the one shown in FIG. 12(*b*) is generated because a gas is encapsulated in the microcapsule 200. When the frequency of the ultrasonic waves irradiated to the microcapsule 200 matches the resonance frequency of the microcapsule, the microcapsule irradiated with the ultrasonic waves undergoes the resonance phenomenon resulting from contraction and expansion due to the presence of the air encapsulated with the medicine in the microcapsule (FIG. 11(*b*)), and a nonlinear echo that includes the transmitted ultrasonic frequency (fundamental wave) and many intensified two-dimensional harmonic signals is generated. This echo is received by the probe 5, detected by the harmonic detection unit 14 similar to the detection of the graphing mode, and thereafter the propagation of the ultrasonic wave progresses and the resonance phenomenon gradually arises in the microcapsules of the deep area. When the transmission wave ultrasonic intensity exceeds the destruction intensity of the microcapsules during the process of this resonance phenomenon, the microcapsules are destroyed, and the medicine encapsulated in the microcapsules is scattered. (FIG. 11(*c*)) Because the resonance phenomenon subsides due to this destruction, the level of the harmonic component rapidly drops.

When the transmission and reception of the ultrasonic waves in the initial direction is concluded, the CPU 13 repeats the transmission and reception and scanning while successively shifting the transmission and reception direction of the ultrasonic waves with respect to the treatment range. Then the fundamental wave echo signal and the harmonic echo signal obtained by the transmission and reception are processed by the Raster processing unit, the CM detection unit and the TI detection unit, and displayed on the color display device as a tomogram, a CM image, and a time intensity curve.

The doctor observes the CM image and the time intensity curve, and stops the ultrasonic scanning for treatment at the point in time when it is confirmed that the flow of the microcapsules to the treatment area has decreased.

Figure 13:
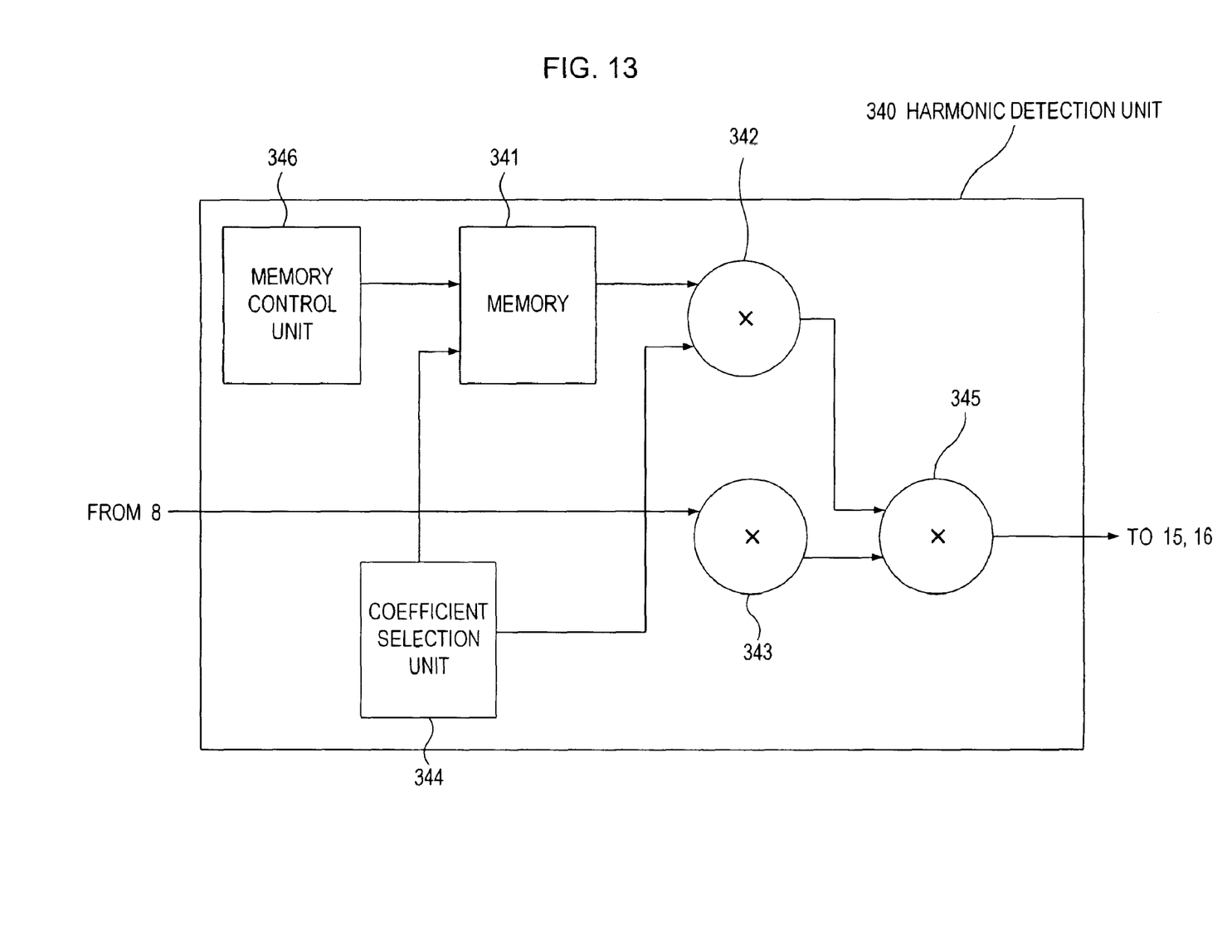
FIG. 13 is a diagram showing a modified example of the harmonic detection unit.

Although an embodiment of the invention has been described above, various modified examples of the invention are also possible. FIG. 13 shows another structural example of the harmonic detection unit. A harmonic detection unit 340 shown in FIG. 13 comprises a memory 341 which comprises a RAM and the like, multipliers 342 and 343, a coefficient selection unit 344, which is configured by a memory such as a ROM, a register and a selector, an adder 345, and a memory control unit 346, which is configured by a counter and a register. When the ultrasonic diagnostic/treatment device shown in FIG. 1 is modified, replacing the harmonic detection unit 14 with this harmonic detection unit 340, it becomes possible for the transmission wave generation unit 1 to generate plural transmission wave pulses of different phases. Transmission wave pulses having a certain phase initially are generated, the echo signals are measured, and the echo signals are stored in the memory 341. Next, ultrasonic beams resulting from the transmission wave pulses of phases different from the previous one are transmitted in the same direction as previously, and the echo signals thereof are measured. The echo signals obtained by this second transmission and reception are inputted to the multiplier 343, and the echo signals of the first time stored in the memory 341 are read out at the same time that the echo signals obtained by this second transmission and reception are inputted to the harmonic detection unit 340 by the control of the memory control unit 346 and inputted to the multiplier 342. The multipliers 342 and 343 conduct multiplication between the coefficient signals outputted from the coefficient selection unit 344 and the inputted echo signals, and output the result to the adder 345. The adder 345 adds the inputted signals together and outputs a synthesized signal. When the echo signal of the first time and the echo signal of the second time are added in the adder 345, because the phases of their fundamentals waves are shifted, negation arises, e.g. when the phase is shifted by δ/2, the fundamental wave is ideally completely negated, and only a nonlinear harmonic remains. This is outputted from the adder 345.

Figure 3:
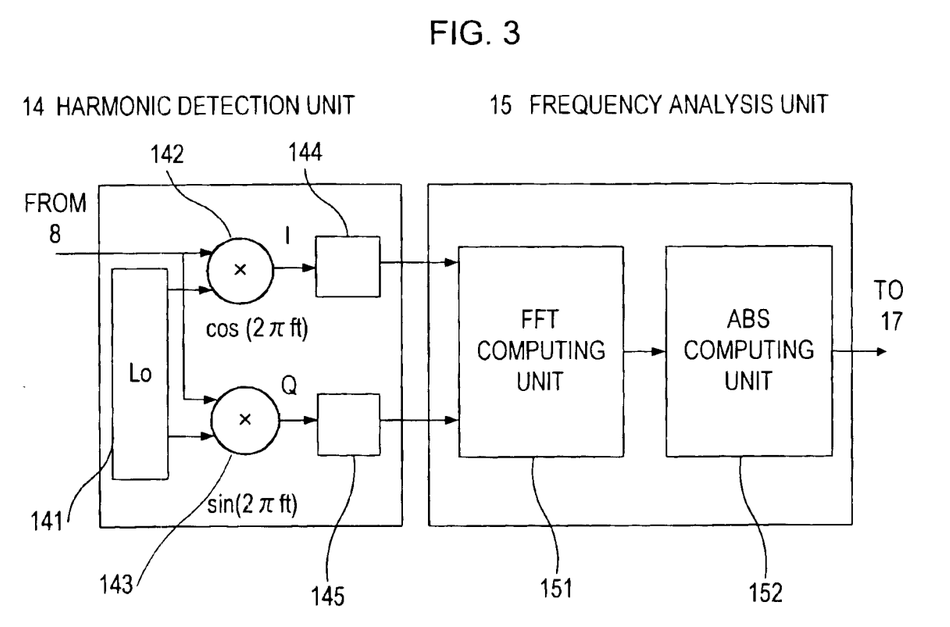
FIG. 3 is a diagram of the harmonic detection unit shown in FIG. 1. It is a block diagram showing the configuration of a frequency analysis unit.

Also, in the embodiment shown in FIG. 1, although an example was described where the frequency analysis was conducted using the FFT computing unit 151 of the frequency analysis unit 15, as shown in FIG. 3, the frequency analysis may also be conducted by wavelet computing means.

Moreover, other modified examples of the invention are possible. For example, in the above embodiment, although an example was described where one type of medicine used for the treatment was used and the microcapsules were injected into the patient, it is also possible to configure a mode that can treat the diseased part using plural types of microcapsules in which respectively different medicines are encapsulated. In this case, treatment is possible so that the intensity and frequency of the transmitted ultrasonic waves are set and stored in advance in the CPU in accordance with the injection order of the medicines, plural treatment modes can be selected with the operation mode selection switch, the doctor determines the concentration of each type of microcapsule flowing to the diseased part with the time intensity curve and the color mapping image, and an operation that switches the intensity and the frequency of the ultrasonic wave following the destruction timing for the respective microcapsules is conducted by selective switching of the treatment mode.

Although an example was described where the intensity and the frequency of the ultrasonic waves used in the treatment were switched and set, it is also possible to operate a setting that varies the focus range of the transmitted ultrasonic wave depending on the size and nature of the diseased part. For example, for a diseased part present over a relatively wide range, the focus range of the ultrasonic waves is set to match the size of the diseased part and the ultrasonic waves are transmitted so that the medicine inside the microcapsules acts on the diseased part in that wide range. For a diseased part requiring that medicine of an even concentration be administered thereto, the focus range that is a conventional sphere may be set to be non-spherical to match the diseased part. In cases where the diseased part is small or side effects of the medicine are strong, the focus range may be set to be smaller so that administration of the medicine is kept at a minimum.

Although an example was described where the diseased part can be treated using, as the microcapsules, plural types of microcapsules in which respectively different medicines are encapsulated, plural ultrasonic diagnostic/treatment devices and injectors of the respective microcapsules may be coordinated so that the plural types of microcapsules are injected at the same time or alternatingly. Due to this control, the doctor need only determine the timing for transmitting the ultrasonic waves for treatment while watching the display unit and can concentrate on operations for the treatment.

As described above, according to the invention, the microcapsules reach the diseased part, and the doctor conducting the ultrasonic treatment can easily determine, by observing the time intensity curve, that the microcapsules have reached an optimum concentration in the diseased part. Also, because the status of movement of the microcapsules to the diseased part is color-mapped and displayed in the ultrasonic diagnostic/treatment device according to the invention, the destruction status of the microcapsules can visually and easily be confirmed by the doctor. Moreover, according to the ultrasonic diagnostic/treatment device of the invention, the administration timing of numerous types of microcapsules becomes easily estimable.

Also, although an example was described where the doctor can determine that the microcapsules have reached an optimum concentration by the display of the time intensity curve, the invention is not limited to the time intensity curve, and all types of representations of information are included, such as schematic drawings representing ultrasonic wave generation after microcapsule destruction, messages, and numerical values of luminance, as long as they are information conveyance means with which the doctor can determine that the microcapsules have become an optimum concentration. Examples informing the doctor by sensory means are also included, for example audio generation means such as a speaker disposed together with the color display unit and generating a chime or other audio message. These modes are all conducted on the basis of monitoring temporal changes in the echo signal amount and comparing the temporal change value with a preset, predetermined standard echo signal value.

Also, when the information conveyance means representing that the microcapsules have reached an optimum concentration are combined as needed, the information representing that the microcapsules have reached an optimum concentration is reliably conveyed to the doctor.

Also, with respect to the display mode of the time intensity curve, the time intensity curve may also be displayed independently, or the tomogram of the organism or an image in which the high-frequency wave from the microcapsules is depicted may be displayed together with the time intensity curve, or switched or superposed with the time intensity curve.

What is claimed is:

1. An ultrasonic diagnostic/treatment device including:
   first ultrasonic wave irradiation means that transmits, to an organism, a first ultrasonic wave signal for obtaining an image and receives a received wave signal corresponding to an echo signal of the first ultrasonic wave signal;
   means that processes the received wave signal to obtain diagnostic information;
   second ultrasonic wave irradiation means that irradiates, the organism with a second ultrasonic wave signal for destroying medicine-containing microcapsules administered to the organism; and
   control means that controls the second ultrasonic wave irradiation means on the basis of the diagnostic information obtained by the first ultrasonic wave irradiation means.

2. The ultrasonic diagnostic/treatment device of claim 1, wherein the control means includes irradiation timing generation means that generates an irradiation timing schedule of the second ultrasonic wave signal using the diagnostic information obtained by the first ultrasonic wave irradiation means.

3. The ultrasonic diagnostic/treatment device of claim 2, wherein the irradiation timing generation means includes image display means that displays an image of the echo signals from the first ultrasonic wave signals comprising a harmonic component of the ultrasonic waves reflected by the microcapsules.

4. The ultrasonic diagnostic/treatment device of claim 2, wherein the irradiation timing generation means includes image display means that displays a tomogram of the organism superposed with an image of the echo signal obtained by the first ultrasonic wave signal comprising a harmonic component of the ultrasonic waves reflected by the microcapsules.

5. The ultrasonic diagnostic/treatment device of claim 2, wherein the irradiation timing generation means includes audio generation means that generates audio relating to the generation of the second ultrasonic wave signal on the basis of temporal changes in the amount of the echo signal changing due to the microcapsules flowing to a diseased part in the organism.

6. The ultrasonic diagnostic/treatment device of claim 2, wherein the irradiation timing generation means includes image display means that displays temporal changes in the amount of the echo signal changing due to the microcapsules flowing to a diseased part in the organism.

7. The ultrasonic diagnostic/treatment device of claim 6, wherein the image display means displays numerical values of the temporal changes in the echo signal amount.

8. The ultrasonic diagnostic/treatment device of claim 6, wherein the image display means displays a message relating to the generation of the second ultrasonic wave signal on the basis of a comparison between temporal changes in the monitored echo signal amount and a preset, predetermined value.

9. The ultrasonic diagnostic/treatment device of claim 6, wherein the image display means includes means that generates a graph of a time intensity curve showing the echo signal amount along one axis and time along the other axis.

10. The ultrasonic diagnostic/treatment device of claim 9, wherein the image display means superposes the graph of a time intensity curve with an image of the echo signal comprising a harmonic component of the ultrasonic waves reflected from the microcapsules or a tomogram of across section of the organism or both in the display.

11. The ultrasonic diagnostic/treatment device of claim 9, wherein the image display means displays in parallel the graph of a time intensity curve and an image of the echo signal comprising a harmonic component of the ultrasonic waves reflected from the microcapsules or a tomogram of a cross section of the organism or both.

12. The ultrasonic diagnostic/treatment device of claim 9, wherein the image display means switches display between the graph of a time intensity curve and an image of the echo signal comprising a harmonic component of the ultrasonic waves reflected from the microcapsules or a tomogram of a cross section of the organism or both.

13. The ultrasonic diagnostic/treatment device of claim 2, wherein the irradiation timing generation means includes image display means that displays undestroyed microcapsules measured by the first ultrasonic wave signal when the ultrasonic wave signal has been switched from the second ultrasonic wave signal to the first ultrasonic wave signal.

14. The ultrasonic diagnostic/treatment device of claim 13, further including means that adjusts the frequency and intensity of the second ultrasonic wave signal on the basis of the undestroyed microcapsules.

15. The ultrasonic diagnostic/treatment device of claim 2, wherein the irradiation timing generation means includes means that freezes the display of an image at a position at which the diseased part of the organism that is to be treated is best displayed by image display means when the ultrasonic wave signal is switched from the first ultrasonic wave signal to the second ultrasonic wave signal.

16. The ultrasonic diagnostic/treatment device of claim 1, wherein the transmission intensity P1 of the first ultrasonic wave signal is $0<P1\ 1[W/cm^2]$ and the transmission intensity P2 of the second ultrasonic wave signal is $0<P2\ 5[W/cm^2]$.

17. The ultrasonic diagnostic/treatment device of claim 1, wherein the ratio of the transmission intensity P1 of the first ultrasonic wave signal and the transmission intensity P2 of the second ultrasonic wave signal is $P1=m \times P2$ (where m is $0<m\ 0.2$).

18. The ultrasonic diagnostic/treatment device of claim 1, wherein the control means controls the focus range of the ultrasonic waves irradiated to the organism from the second ultrasonic wave irradiation means.

19. An ultrasonic diagnostic/treatment device including:
a probe that transmits ultrasonic waves to an organism to which medicine-containing microcapsules have been administered and that receives the echo thereof;
means that sets, in a transmission wave signal generation unit, a first ultrasonic wave signal for obtaining an image of the organism;
means that receives the echo corresponding to the first ultrasonic wave signal as a signal and conducts processing for image-displaying the echo signal;
means that acquires the processed echo signal as diagnostic information;
means that sets, in the transmission wave signal generation unit, a second ultrasonic wave signal that can destroy the microcapsules;
means that causes the probe to transmit the second ultrasonic wave signal to the organism; and
means that switches between the first ultrasonic wave signal and the second ultrasonic wave signal on the basis of the obtained diagnostic information.

20. An ultrasonic diagnostic/treatment device including:
first ultrasonic wave irradiation means that transmits, to an organism to which at least two different types of medicine-containing microcapsules have been administered, a first ultrasonic wave signal for obtaining an image and receives a received wave signal corresponding to an echo signal of the first ultrasonic wave signal;
means that processes the received wave signal to obtain diagnostic information;
second ultrasonic wave irradiation means that irradiates the organism with a second ultrasonic wave signal for destroying the microcapsules administered to the organism; and
control means that controls the second ultrasonic wave irradiation means on the basis of the obtained diagnostic information.

21. The ultrasonic diagnostic/treatment device of claim 20, further including
means that inputs the order in which the plural types of microcapsules are injected and the intensity and frequency of ultrasonic waves transmitted to each of the microcapsules,
means that stores the inputted injection order and the intensity and frequency of the ultrasonic waves per microcapsule, and
control means that controls the second ultrasonic wave irradiation means according to the second ultrasonic wave signal that is set for each microcapsule on the basis of the stored injection order and the intensity and frequency of the ultrasonic waves.

22. The ultrasonic diagnostic/treatment device of claim 21, further including means that controls the injector on the basis of the order set by the input means.

23. An ultrasonic diagnostic/treatment device including:
a probe that transmits ultrasonic waves to an organism to which at least two types of medicine-containing microcapsules have been administered and that receives the echo thereof;
means that sets, in a transmission wave signal generation unit, a first ultrasonic wave signal for obtaining an image of the organism;
means that receives the echo corresponding to the first ultrasonic wave signal as a signal and conducts processing for image-displaying the echo signal;
means that acquires the processed echo signal as diagnostic information;
means that sets, in the transmission wave signal generation unit, a second ultrasonic wave signal that can destroy the microcapsules;
means that causes the probe to transmit the second ultrasonic wave signal to the organism on the basis of the acquired diagnostic information; and
means that switches between the first ultrasonic wave signal and the second ultrasonic wave signal on the basis of the obtained diagnostic information.

24. An ultrasonic diagnostic and treatment method including the steps of:
transmitting, to an organism, a first ultrasonic wave signal for obtaining an image and receiving a received wave signal corresponding to the echo signal of the first ultrasonic wave signal;

processing the received wave signal to obtain diagnostic information; and controlling a second ultrasonic wave signal for destroying medicine-containing microcapsules administered to the organism on the basis of the obtained diagnostic information.

25. The ultrasonic diagnostic and treatment method of claim 24, wherein the control step includes an irradiation timing generation step for setting the timing of transmission of the second ultrasonic wave signal using the obtained diagnostic information.

26. The ultrasonic diagnostic and treatment method of claim 25, wherein the irradiation timing generation step includes a step for displaying an image of the echo signal from the first ultrasonic wave signal, comprising a harmonic component of the ultrasonic waves reflected by the microcapsules.

27. The ultrasonic diagnostic and treatment method of claim 26, wherein the image display step includes a step for generating a graph of a time intensity curve showing the echo signal amount on one axis and time on the other axis, to display the generated graph.

28. The ultrasonic diagnostic and treatment method of claim 27, wherein the image display step superposes display of the graph of a time intensity curve with an image of the echo signal comprising a harmonic component of the ultrasonic waves reflected from the microcapsules or a tomogram of a cross section of the organism or both.

29. The ultrasonic diagnostic and treatment method of claim 27, wherein the image display step displays in parallel the graph of a time intensity curve and an image of the echo signal comprising a harmonic component of the ultrasonic waves reflected from the microcapsules or a tomogram of across section of the organism or both.

30. The ultrasonic diagnostic and treatment method of claim 27, wherein the image display step switches display between the graph of a time intensity curve and an image of the echo signal comprising a harmonic component of the ultrasonic waves reflected from the microcapsules or a tomogram of a cross section of the organism or both.

31. The ultrasonic diagnostic and treatment method of claim 25, wherein the irradiation timing generation step includes a step that freezes display of the image at the position at which the diseased part of the organism that is to be treated is best displayed by image display means when the ultrasonic wave signal has been switched from the first ultrasonic wave signal to the second ultrasonic wave signal.

32. The ultrasonic diagnostic and treatment method of claim 25, wherein the irradiation timing generation step includes a step for superposing and displaying a tomogram of the organism with an image of the echo signal obtained by the first ultrasonic wave signal comprising a harmonic component of the ultrasonic waves reflected by the microcapsules.

33. The ultrasonic diagnostic and treatment method of claim 25, wherein the irradiation timing generation step includes a step for generating audio relating to the generation of the second ultrasonic wave signal on the basis of temporal changes in the amount of the echo signal changing due to the microcapsules flowing to a diseased part in the organism.

34. The ultrasonic diagnostic and treatment method of claim 25, wherein the irradiation timing generation includes a step for displaying temporal changes in the amount of the echo signal changing due to the microcapsules flowing to a diseased part in the organism.

35. The ultrasonic diagnostic and treatment method of claim 24, wherein a transmission intensity P1 of the first ultrasonic wave signal is 0<P1 1[W/cm$^2$] and a transmission intensity P2 of the second ultrasonic wave signal is 1<P2 5[W/cm$^2$].

36. The ultrasonic diagnostic and treatment method of claim 24, wherein the ratio of the transmission intensity P1 of the first ultrasonic wave signal and the transmission intensity P2 of the second ultrasonic wave signal is P1=m× P2 (where m is 0<m 0.2).

37. The ultrasonic diagnostic and treatment method of claim 24, further including a step for controlling the focus range of the second ultrasonic wave irradiation means.

38. An ultrasonic diagnostic and treatment method including the steps of:

setting, in a transmission wave signal generation unit, a first ultrasonic wave signal to be transmitted to an organism to which medicine-containing microcapsules have been administered, and by receiving the echo thereof obtaining an image of the organism;

receiving the echo corresponding to the first ultrasonic wave signal as a signal and conducting processing for image-displaying the echo signal;

acquiring the processed echo signal as diagnostic information;

setting, in the transmission wave signal generation unit, a second ultrasonic wave signal that can destroy the microcapsules;

transmitting the second ultrasonic wave signal to the organism; and switching between the first ultrasonic wave signal and the second ultrasonic wave signal on the basis of the obtained diagnostic information.

39. An ultrasonic diagnostic and treatment method including the steps of:

transmitting, to an organism, a first ultrasonic wave signal for obtaining an image and receiving a received wave signal corresponding to the echo signal of the first ultrasonic wave signal;

processing the received wave signal to obtain diagnostic information;

transmitting, to the organism, a second ultrasonic wave signal for destroying at least two types of medicine-containing microcapsules that have been administered to the organism;

switching, on the basis of the obtained diagnostic information, from the first ultrasonic wave signal to the second ultrasonic wave signal for destroying at least two types of medicine-containing microcapsules that have been administered to the organism, and transmitting the second ultrasonic wave signal to the organism.

40. The ultrasonic diagnostic and treatment method of claim 39, further including the steps of inputting an order in which the plural types of microcapsules are injected and the intensity and frequency of ultrasonic waves transmitted for each of the microcapsules, storing the inputted injection order and the intensity and frequency of the ultrasonic waves per microcapsule, and controlling the second ultrasonic wave irradiation means according to the second ultrasonic wave signal that is set for each microcapsule on the basis of the stored injection order and the intensity and frequency of the ultrasonic waves.

41. The ultrasonic diagnostic and treatment method of claim 40, further including a step for controlling the injector on the basis of the order set by the input step.

42. An ultrasonic diagnostic and treatment method including the steps of:

transmitting ultrasonic waves to an organism to which at least two types of medicine-containing microcapsules have been administered, receiving an echo thereof, and setting, in a transmission wave signal generation unit, a first ultrasonic wave signal for obtaining an image of the organism;

receiving the echo corresponding to the first ultrasonic wave signal as a signal and conducting processing for image-displaying the echo signal;

acquiring the processed echo signal as diagnostic information;

setting, in the transmission wave signal generation unit, a second ultrasonic wave signal that can destroy for each microcapsule;

transmitting the second ultrasonic wave signal to the organism; and switching between the first ultrasonic wave signal and the second ultrasonic wave signal on the basis of the obtained diagnostic information.

\* \* \* \* \*